(12) United States Patent
Gowda et al.

(10) Patent No.: US 9,403,029 B2
(45) Date of Patent: Aug. 2, 2016

(54) SYSTEMS AND METHODS FOR THERMAL THERAPY

(75) Inventors: Ashok Gowda, Houston, TX (US); Roger McNichols, Pearland, TX (US)

(73) Assignee: Visualase, Inc., Houston, TX (US)

( * ) Notice: Subject to any disclaimer, the term of this patent is extended or adjusted under 35 U.S.C. 154(b) by 1437 days.

(21) Appl. No.: 12/418,562

(22) Filed: Apr. 3, 2009

(65) Prior Publication Data

US 2009/0198309 A1 Aug. 6, 2009

Related U.S. Application Data

(63) Continuation-in-part of application No. 12/176,310, filed on Jul. 18, 2008, now abandoned.

(60) Provisional application No. 61/042,199, filed on Apr. 3, 2008, provisional application No. 60/950,536, filed on Jul. 18, 2007.

(51) Int. Cl.
*A61B 18/18* (2006.01)
*A61N 5/06* (2006.01)
*A61N 5/067* (2006.01)

(52) U.S. Cl.
CPC .......... *A61N 5/0601* (2013.01); *A61B 18/1815* (2013.01); *A61N 2005/067* (2013.01); *A61N 2005/0643* (2013.01)

(58) Field of Classification Search
CPC ........ A61B 18/18; A61B 18/04; A61B 19/00; A61B 5/05; A61B 8/00; A61B 5/00; A61B 19/20; A61B 6/0421; A61B 18/1206; A61F 2/00; G01N 31/00; A61N 5/0601
USPC .............. 606/41, 34, 27, 21, 130, 2; 607/102; 702/22; 600/414, 447, 549, 417, 429; 604/116
See application file for complete search history.

(56) References Cited

U.S. PATENT DOCUMENTS 4,140,130 A 2/1979 Storm, III
4,362,161 A 12/1982 Reimels et al.
(Continued)

FOREIGN PATENT DOCUMENTS

CA 2548226 A1 5/2005
DE 4137983 A1 6/1992
(Continued)

OTHER PUBLICATIONS

Communication pursuant to Article 94(3) EPC dated Sep. 12, 2014 for European Application No. 09 726 951.8-1652.
(Continued)

*Primary Examiner* — Gary Jackson
*Assistant Examiner* — Victor Shapiro
(74) *Attorney, Agent, or Firm* — Harness, Dickey (57) ABSTRACT

The present invention is directed to systems and methods for thermal therapy, especially to detection-guided, -controlled, and temperature-modulated interstitial thermal therapy. Thermal therapy may be used to treat the tissues of a patient. In the case of interstitial thermal therapy, energy is applied to generate heating of the tissue to affect treatment, such as, for example, thermally inducing tissue damage (e.g. thermally-induced tissue necrosis), which may be useful in treating tumors and/or other diseased tissues. Since targets for thermal therapy are internal to the patient, the use of detection guidance may be useful in locating and monitoring treatment of a target tissue.

19 Claims, 4 Drawing Sheets

(56) References Cited

U.S. PATENT DOCUMENTS

| | | |
|---|---|---|
| 4,466,697 A | 8/1984 | Daniel |
| 4,515,165 A | 5/1985 | Carroll |
| 4,554,925 A | 11/1985 | Young |
| 4,585,298 A | 4/1986 | Mori |
| 4,608,977 A * | 9/1986 | Brown .................... 606/130 |
| 4,633,875 A | 1/1987 | Turner |
| 4,638,800 A | 1/1987 | Michel |
| 4,660,952 A | 4/1987 | Toyoda et al. |
| 4,669,467 A | 6/1987 | Willett et al. |
| 4,693,556 A | 9/1987 | McCaughan, Jr. |
| 4,785,815 A | 11/1988 | Cohen |
| 4,832,024 A | 5/1989 | Boussignac et al. |
| 4,852,567 A | 8/1989 | Sinofsky |
| 4,862,887 A | 9/1989 | Weber et al. |
| 4,923,459 A * | 5/1990 | Nambu .................... 606/130 |
| 4,959,063 A | 9/1990 | Kojima |
| 4,960,109 A * | 10/1990 | Lele ...................... 600/549 |
| 4,986,628 A | 1/1991 | Lozhenko et al. |
| 5,042,980 A | 8/1991 | Baker et al. |
| 5,061,265 A | 10/1991 | Abela et al. |
| 5,074,632 A | 12/1991 | Potter |
| 5,116,345 A | 5/1992 | Jewell et al. |
| 5,151,096 A | 9/1992 | Khoury |
| 5,169,396 A | 12/1992 | Dowlatshahi et al. |
| 5,196,005 A | 3/1993 | Doiron et al. |
| 5,207,669 A | 5/1993 | Baker et al. |
| 5,219,346 A | 6/1993 | Wagnieres et al. |
| 5,222,953 A | 6/1993 | Dowlatshahi |
| 5,246,436 A | 9/1993 | Rowe |
| 5,269,777 A | 12/1993 | Doiron et al. |
| 5,281,232 A * | 1/1994 | Hamilton ............ A61B 6/0421 600/429 |
| 5,292,320 A | 3/1994 | Brown et al. |
| 5,303,324 A | 4/1994 | Lundahl |
| 5,307,812 A | 5/1994 | Hardy et al. |
| 5,312,392 A | 5/1994 | Hofstetter et al. |
| 5,323,779 A | 6/1994 | Hardy et al. |
| 5,327,884 A | 7/1994 | Hardy et al. |
| 5,330,465 A | 7/1994 | Doiron et al. |
| 5,337,381 A | 8/1994 | Biswas et al. |
| 5,348,552 A | 9/1994 | Nakajima et al. |
| 5,363,458 A | 11/1994 | Pan et al. |
| 5,368,031 A | 11/1994 | Cline et al. |
| 5,373,571 A | 12/1994 | Reid et al. |
| 5,429,635 A | 7/1995 | Purcell, Jr. et al. |
| 5,431,647 A | 7/1995 | Purcell, Jr. et al. |
| 5,441,497 A | 8/1995 | Narciso, Jr. |
| 5,454,807 A | 10/1995 | Lennox et al. |
| 5,483,961 A * | 1/1996 | Kelly .................... A61B 19/20 600/417 |
| 5,496,308 A | 3/1996 | Brown et al. |
| 5,501,655 A | 3/1996 | Rolt et al. |
| 5,520,681 A | 5/1996 | Fuller et al. |
| 5,530,780 A | 6/1996 | Ohsawa |
| 5,536,265 A | 7/1996 | van den Bergh et al. |
| 5,545,161 A | 8/1996 | Imran |
| 5,607,421 A | 3/1997 | Jeevanandam et al. |
| 5,647,361 A | 7/1997 | Damadian |
| 5,651,785 A | 7/1997 | Abela et al. |
| 5,665,095 A * | 9/1997 | Jacobson ............ A61B 19/201 604/116 |
| 5,688,263 A | 11/1997 | Hauptmann et al. |
| 5,754,717 A | 5/1998 | Esch |
| 5,792,100 A | 8/1998 | Shantha |
| 5,800,557 A | 9/1998 | Elhami et al. |
| 5,807,390 A | 9/1998 | Fuller et al. |
| 5,824,005 A | 10/1998 | Motamedi et al. |
| 5,830,196 A | 11/1998 | Hicks |
| 5,843,073 A | 12/1998 | Sinofsky |
| 5,855,577 A | 1/1999 | Murphy-Chutorian et al. |
| 5,861,020 A | 1/1999 | Schwarzmaier |
| 5,871,521 A | 2/1999 | Kaneda et al. |
| 5,906,606 A | 5/1999 | Chee et al. |
| 5,908,415 A | 6/1999 | Sinofsky |
| 5,946,441 A | 8/1999 | Esch |
| 5,947,959 A | 9/1999 | Sinofsky |
| 5,978,541 A | 11/1999 | Doiron et al. |
| 5,997,571 A | 12/1999 | Farr et al. |
| 6,004,315 A | 12/1999 | Dumont |
| 6,039,728 A | 3/2000 | Berlien et al. |
| 6,048,359 A * | 4/2000 | Biel .................. A61N 5/0601 606/2 |
| 6,071,302 A | 6/2000 | Sinofsky et al. |
| 6,102,905 A | 8/2000 | Baxter et al. |
| 6,106,514 A | 8/2000 | O'Donnell, Jr. |
| 6,113,593 A * | 9/2000 | Tu et al. ...................... 606/34 |
| 6,128,522 A | 10/2000 | Acker |
| 6,174,308 B1 * | 1/2001 | Goble ................ A61B 18/1206 128/898 |
| 6,212,426 B1 | 4/2001 | Swanson |
| 6,270,492 B1 | 8/2001 | Sinofsky |
| 6,283,958 B1 | 9/2001 | Vogl et al. |
| 6,311,084 B1 | 10/2001 | Cormack et al. |
| 6,315,776 B1 | 11/2001 | Edwards et al. |
| 6,343,174 B1 | 1/2002 | Neuberger |
| 6,361,530 B1 | 3/2002 | Mersch |
| 6,381,483 B1 | 4/2002 | Hareyama et al. |
| 6,383,179 B1 | 5/2002 | Neuberger |
| 6,418,252 B1 | 7/2002 | Maitland |
| 6,418,337 B1 | 7/2002 | Torchia et al. |
| 6,503,246 B1 | 1/2003 | Har-Shai et al. |
| 6,506,189 B1 * | 1/2003 | Rittman et al. ................ 606/41 |
| 6,542,767 B1 | 4/2003 | McNichols et al. |
| 6,554,824 B2 | 4/2003 | Davenport et al. |
| 6,575,969 B1 * | 6/2003 | Rittman et al. ................ 606/41 |
| 6,576,163 B2 | 6/2003 | Mersch |
| 6,802,838 B2 | 10/2004 | Loeb et al. |
| 6,996,478 B2 * | 2/2006 | Sunshine et al. ................ 702/22 |
| 7,171,253 B2 | 1/2007 | Dowlatshahi |
| 7,270,656 B2 | 9/2007 | Gowda et al. |
| 7,274,847 B2 | 9/2007 | Gowda et al. |
| 7,344,529 B2 | 3/2008 | Torchia et al. |
| 7,412,141 B2 | 8/2008 | Gowda et al. |
| 7,609,927 B2 | 10/2009 | Gowda et al. |
| 7,699,838 B2 | 4/2010 | Breen et al. |
| 7,780,679 B2 | 8/2010 | Bobo, Sr. et al. |
| 7,871,406 B2 * | 1/2011 | Nields et al. .................... 606/27 |
| 7,909,817 B2 | 3/2011 | Griffin et al. |
| 8,211,095 B2 | 7/2012 | Gowda et al. |
| 8,851,080 B2 | 10/2014 | Gowda et al. |
| 2002/0193800 A1 | 12/2002 | Kienzle et al. |
| 2005/0065515 A1 | 3/2005 | Jahng |
| 2005/0075649 A1 | 4/2005 | Bova et al. |
| 2006/0084867 A1 | 4/2006 | Tremblay et al. |
| 2006/0149280 A1 | 7/2006 | Harvie et al. |
| 2006/0184163 A1 | 8/2006 | Breen et al. |
| 2007/0239150 A1* | 10/2007 | Zvuloni et al. .................... 606/21 |
| 2007/0249938 A1* | 10/2007 | Shields ...................... 600/447 |
| 2008/0200798 A1* | 8/2008 | Eklund et al. ................ 600/414 |
| 2009/0198309 A1 | 8/2009 | Gowda et al. |
| 2009/0292279 A1 | 11/2009 | Bliweis et al. |
| 2015/0094698 A1 | 4/2015 | Gowda et al. |

FOREIGN PATENT DOCUMENTS

| | | |
|---|---|---|
| EP | 0361762 A2 | 4/1990 |
| EP | 1689464 A2 | 8/2006 |
| EP | 2285307 A1 | 2/2011 |
| EP | 2412403 A2 | 2/2012 |
| JP | 2000217835 A | 8/2000 |
| JP | 2001046523 A | 2/2001 |
| JP | 2011516184 A | 5/2011 |
| WO | WO-8903665 A1 | 5/1989 |
| WO | WO-9614880 A1 | 5/1996 |
| WO | WO-9932184 A1 | 7/1999 |
| WO | WO-9942044 A1 | 8/1999 |
| WO | WO-0195822 A2 | 12/2001 |
| WO | WO-0200298 A1 | 1/2002 |
| WO | WO-0218011 A1 | 3/2002 |
| WO | WO-03065880 A2 | 8/2003 |
| WO | WO-2005046753 A2 | 5/2005 |
| WO | WO-2006055554 A2 | 5/2006 |
| WO | WO-2006078677 A2 | 7/2006 |
| WO | WO-2007005830 A2 | 1/2007 |

(56) References Cited

FOREIGN PATENT DOCUMENTS

| WO | WO 2007086056 A2 * | 8/2007 |
| WO | WO-2007086056 A2 | 8/2007 |
| WO | WO-2007090288 A1 | 8/2007 |
| WO | WO-2009060394 A1 | 5/2009 |
| WO | WO-2009124301 A1 | 10/2009 |

OTHER PUBLICATIONS

International Preliminary Report on Patentability with Written Opinion mailed on May 30, 2007 for PCT/US04/37244 claiming benefit of U.S. Appl. No. 10/703,304, filed Nov. 7, 2003.

International Search Report with Written Opinion mailed on Apr. 10, 2007 for PCT/US04/37244 claiming benefit of U.S. Appl. No. 10/703,304, filed Nov. 7, 2003.

U.S. Appl. No. 10/208,222, filed Jul. 30, 2002 entitled "Cooled Tip Laser Catheter for Sensing and Ablation of Cardiac Arrhythmias."

Weber et al., "Laser versus Radiofrequency Catheter Ablation of Ventricular Myocardium in Dogs: A Comparative Test," Cardiology, vol. 88, 1997, pp. 346-352.

Welch et al., "Evaluation of Cooling Techniques for the Protection of the Epidermis During Nd: YAG Laser Irradiation of the Skin," in Neodymium-YAG Laser in Medicine and Surgery, S.N. Joffe, Ed. New York: Elsevier, 1983, pp. 196-204.

International Preliminary Report and Written Opinion mailed on May 10, 2010 for PCT/US2009/39568 claiming benefit of U.S. Appl. No. 61/042,199, filed Apr. 3, 2008.

International Search Report and Written Opinion mailed on Jul. 16, 2009 for PCT/US2009/39568 claiming benefit of U.S. Appl. No. 61/042,199, filed Apr. 3, 2008.

* cited by examiner

SYSTEMS AND METHODS FOR THERMAL THERAPY

CROSS-REFERENCE TO RELATED APPLICATIONS

This application claims the benefit of U.S. provisional patent application Ser. No. 61/042,199, filed Apr. 3, 2008, entitled "SYSTEMS AND METHODS FOR THERMAL THERAPY", the entire contents of which are hereby incorporated by reference.

This application is a continuation-in-part of co-pending U.S. patent application, Ser. No. 12/176,310, filed Jul. 18, 2008, entitled "LIGHT DIFFUSING FIBER AND METHOD OF USE", which claims priority to U.S. provisional patent application, Ser. No. 60/950,536, filed Jul. 18, 2007, entitled "LIGHT DIFFUSING LASER FIBER AND METHOD OF USE", the entire contents of which are hereby incorporated by reference.

FIELD OF THE INVENTION

The present invention relates to systems and methods for thermal therapy, especially to detection-guided, -controlled, and temperature-modulated interstitial thermal therapy.

BACKGROUND OF THE INVENTION

In the medical industry, undesirable lesions can be treated through their removal. It is known to have a practitioner, such as a doctor, physically remove such lesions through surgery. It is also known to have a practitioner destroy lesions by controlling an application of heat local to the lesion. Known processes whereby a practitioner destroys the lesion by using heat require the practitioner to control the process based on visual data and temperature data. Based upon this information, the practitioner will modify the heat source to change an attribute of the heat, such as its location, direction, and intensity. The proper application of the heat delivery process is dependent upon the ability of the practitioner to interpret available visual and temperature data, and to implement an appropriate treatment in response. As a result, the ability to control processes in a predictable manner varies between practitioners, and even varies instance-to-instance for a given practitioner.

SUMMARY OF THE INVENTION

The present invention is directed to systems and methods for thermal therapy, for example, to detection-guided, -controlled, and/or temperature-modulated interstitial thermal therapy. Thermal therapy may be used to treat the tissues of a patient by transferring energy, such as applying energy and/or removing energy. In the case of interstitial thermal therapy, energy is applied to generate a temperature change in the tissue to affect treatment, such as, for example, thermally inducing tissue damage (e.g. thermally-induced tissue necrosis), which may be useful in treating tumors and/or other diseased tissues. Since targets for thermal therapy are internal to the patient, the use of image and/or a form of detection guidance may be useful and/or desirable in locating and monitoring treatment of a target tissue.

In one aspect of the present invention, a thermal therapy system includes at least one detection device, at least one treatment device and at least one control system. In one embodiment, a treatment device may be inserted into and/or in the vicinity of the body of a patient and monitored by the detection device for proper placement near a target tissue. A treatment device may generally be an energy delivery device such as, for example, a laser probe, a radio frequency (RF) probe, a microwave device, an electromagnetic antenna, an ultrasound probe, a brachytherapy device, and/or any other appropriate energy delivery device. Treatment devices may also include, but are not limited to, biopsy and/or material removal devices, material introducing devices such as catheters and/or injection devices, target access devices, and/or any other appropriate device. In general, an energy delivery device may be selected for compatibility with a given detection device and/or for a particular type of treatment. A detection device may employ, but is not limited to, a magnetic resonance imaging (MRI), ultrasound imaging, X-ray or other electromagnetic imaging, positron emission tomography (PET) imaging, and/or any other appropriate imaging and/or detection modality. In general, an imaging and/or detection modality capable of detecting and/or mapping temperature responses and/or thermally- and/or energy-induced changes to tissues may be utilized.

The treatment device may be an energy delivery device in communication with a control system which may also receive information from a detection device. The control system may generally incorporate a predictive and/or adaptive treatment modulation in a feedback response manner with the detection device and treatment device if desired. In an exemplary aspect, the control system, for example, may control at least one treatment device to transfer, for example, a predetermined amount of energy between the treatment device and at least a portion of a target. In an exemplary embodiment, the control system utilizes information about the target from the detection device, which may, for example, contain temperature-sensitive information and/or spatially-resolved information about at least a portion of the target. The control system and/or a user may then determine a preselected amount of energy to transfer between a treatment device and at least a portion of the target based at least in part on the information from the detection device. The energy may then be transferred by at least one treatment device and the effect on the target may then be determined by a detection device. The control system may further store information on previous energy transfers, such as over the general course of a therapy and/or treatment, and may generally base an amount of energy to be transferred at least in part on previous energy transfer information. Previous information may be stored by the control system in, for example, a memory module and/or other information storage device and/or system. In some embodiments, multiple energy transfers may be utilized.

In general, a thermal therapy system may be utilized to deliver energy to a target tissue such that the tissue may form a lesion by thermally-induced necrosis. This may be useful and/or desirable in treating harmful tissue formations such as, for example, tumors.

In an exemplary embodiment, the treatment device is a laser with a fluid circulation probe. In general, the probe may include an optical fiber and/or other light transporting medium, and may also include a diffusing and/or targeting element for placement of the energy delivered through the light transporting medium from the laser. The fluid circulation in the probe may be used to affect the temperature of the probe and/or the tissue surrounding the probe by circulating fluid of a desired temperature. The temperature of the fluid may be varied to determine the temperature effect on the probe and/or tissue. The flow characteristics of the fluid and energy output of the laser may be determined by the control system such that it may modulate the energy delivery characteristics of the laser to the tissue.

The control system may receive temperature and/or spatial information from a detection device that may detect features and/or changes to the tissues of a patient. The control system may then utilize the information to monitor the progress of a treatment, if desired. In an exemplary embodiment, the treatment device may be a laser. In one embodiment, the device may be a laser with a fluid circulation probe. In general, the probe may include an optical fiber and/or other light transporting medium, and may also include a diffusing and/or targeting element for placement of the energy delivered through the light transporting medium from the laser. The fluid circulation in the probe may be used to affect the temperature of the probe and/or the tissue surrounding the probe by circulating fluid of a desired temperature. The temperature of the fluid may be varied to determine the temperature effect on the probe and/or tissue. The flow characteristics of the fluid and energy output of the laser may be determined by the control system such that it may modulate the energy delivery characteristics of the laser to the tissue.

In some embodiments, the circulating fluid may be utilized to cool the probe and the surrounding tissue. This may be useful in protecting the probe from thermal damage and may also be utilized to help minimize carbonized tissue formation around the probe during treatment, such that the energy being delivered may reach further from the probe.

In other embodiments, the circulating fluid may also be utilized to raise the temperature of the tissue surrounding the probe before and/or during treatment such that, for example, the tissue may reach a given temperature faster during energy delivery by the probe. The temperature may also be raised if the control system determines that insufficient heating is occurring in the tissue to affect treatment, if desired. Raising the temperature of the tissue may also generally enhance the size of the ablated volume as a smaller increase in temperature may be required by energy delivery from the treatment device, particularly at distances further away from the treatment device.

The fluid may be circulated at a constant rate or it may be circulated at a variable rate, which may include periods of no circulation, during the course of a treatment. The temperature of the fluid may also be varied during the course of a treatment.

In some embodiments, the temperature in the locality of the tissue for treatment may be altered by altering the temperature of the circulatory flow and/or surrounding tissue. This may be accomplished through a variety of methods, which may include, but are not limited to, introducing temperature controlled fluid into the circulatory flow, such as through a nearby blood vessel; altering the temperature of the circulatory flow by contact with a closed temperature controlled object, such as a closed catheter which may contain circulating temperature controlled fluid; contacting the nearby tissue with a temperature controlled object or material, such as a hot or cold pad; and/or any other appropriate method. For example, a temperature controlled energy delivery device and/or heating element may be placed in a blood vessel which may be in proximity to and/or supply a tissue for treatment.

In still other embodiments, the thermal therapy system may incorporate multiple treatment devices, which may be the same or different. The treatment devices may be controlled as a group or they may be individually controlled. The treatment devices may be spatially oriented in or near a tissue for treatment and may be utilized to affect treatment in a spatially controlled manner. The treatment devices may, for example, be targeted in particular directions for coverage of a treatment area. The treatment devices may also be controlled in a temporal manner by controlling the activation and/or modulation of each device in a time-dependent manner.

In an exemplary embodiment, the multiple treatment devices may be laser probes with fluid circulation, as discussed above, and may be individually modulated by the control system. The laser probes may, for example, be spatially oriented in or near a tissue for treatment to optimize and/or increase the volume being treated. This may be used, for example, to increase the overall size of a thermally generated lesion. Each laser probe may also be targeted such that energy delivery may be substantially confined to a given volume. The fluid circulation characteristics of each laser probe may also be individually modulated, as discussed above.

The control system of the thermal therapy system may incorporate predictive and/or adaptive treatment modulation, as noted above. In one embodiment, the control system may generate a predictive model of a treatment based on known and/or assumed parameters, and may calculate an appropriate treatment course, such as, for example, applying energy to a tissue at a particular rate and/or duration based on the predicted model. The control system may then monitor the progress of treatment by receiving information from a detection device, and/or it may then adapt to the measured progress of the treatment by entering and/or altering parameters in the predicted model to aid in generating a more accurate model, after which the control system may apply a modulation to the treatment, such as, for example, an alteration to the energy delivery characteristics of a treatment device.

The thermal therapy system may incorporate safety systems. In one embodiment, the control system of a thermal therapy system may shut down the treatment device and/or warn the user of a detected safety parameter. The control system may, for example, shut down the treatment device in response to a detected temperature above a given level in the information provided by a detection device. This may be useful in detecting failures in a treatment device, such as, for example, a laser light transport medium breaking and/or otherwise overheating past a design limitation. This may also be useful by halting treatment if the temperature of the tissue being treated and/or nearby tissue exceeds a given safety threshold.

Communication between devices as used herein may include physical contact, physical connection, wired or wireless connection, or integral with each other.

The present invention together with the above and other advantages may best be understood from the following detailed description of the embodiments of the invention illustrated in the drawings.

DETAILED DESCRIPTION OF THE INVENTION

The detailed description set forth below is intended as a description of the presently exemplified systems, devices and methods provided in accordance with aspects of the present invention, and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any systems, methods, devices and materials similar or equivalent to those described herein can be used in the practice or testing of the invention, the exemplified methods, systems, devices and materials are now described.

The present invention is directed to systems and methods for thermal therapy that may be used to treat the tissues of a patient by applying energy and/or removing energy. In the case of interstitial thermal therapy, energy is applied to generate a temperature change of the tissue to affect treatment, such as, for example, thermally inducing tissue damage (e.g. thermally-induced tissue necrosis), which may be useful in treating tumors and/or other diseased tissues. Since targets for thermal therapy are internal to the patient, the use of image and/or a form of detection guidance may be useful in locating and/or monitoring treatment of a target tissue.

In general, thermal therapy may be defined as a treatment that alters the temperatures or temperature profile of a target, more for example, to the application and/or removal of energy from a target to affect a temperature change or temperature profile change. This may generally include heating, cooling and/or dynamic combinations thereof. Thermal therapy may generally be accomplished through the energy delivery characteristics of a treatment device or devices. Energy delivery characteristics may generally refer to the rate of energy application and/or removal from a target, and the factors contributing to the rate. Energy delivery devices may in general refer to devices for altering and/or maintaining the temperature of a target, such as devices that apply energy to a target and/or devices that remove energy from a target. It may also be appreciated that devices useful for applying and/or delivering energy may be useful for removal of energy. In addition, for example, the same device may be useful for simultaneous applying and removal of energy. Also, transferring of energy refers to applying and/or delivering energy and may also refer to removal of energy.

One example of thermal therapy is laser interstitial thermal therapy (LITT). LITT employs a laser energy source which transmits light through a light transmitting medium such as a fiber optic to a probe at a target tissue. The probe may target the delivery of energy from the laser to the tissue through a variety of methods, which may include, for example, focusing, diffusing/scattering, reflecting and/or otherwise directing the light from the laser. LITT is generally performed using optical radiation in the near-infrared wavelength range, from, for example, about 700-2000 nm, though when appropriate chromophores are available, visible wavelengths may also be used. When light is absorbed by the tissue, the energy from the photons may be converted into inter- and intra-molecular energy and results in generation of heat within the tissue. At temperatures of 100 degrees Celsius or more, water in the tissue and in the intracellular compartments may vaporize and lead to rupture or explosion of cells or tissue components. At temperatures above 60 degrees Celsius, proteins and cellular components of the tissue become severely denatured and coagulate leading to cell and tissue death. At somewhat lower temperatures, generally above 45 degrees Celsius, prolonged exposure leads to the thermal denaturation of non-stabilized proteins such as enzymes. Though cell death may not be immediate, destruction of critical enzymes may lead eventually to cell death.

Figure 1:
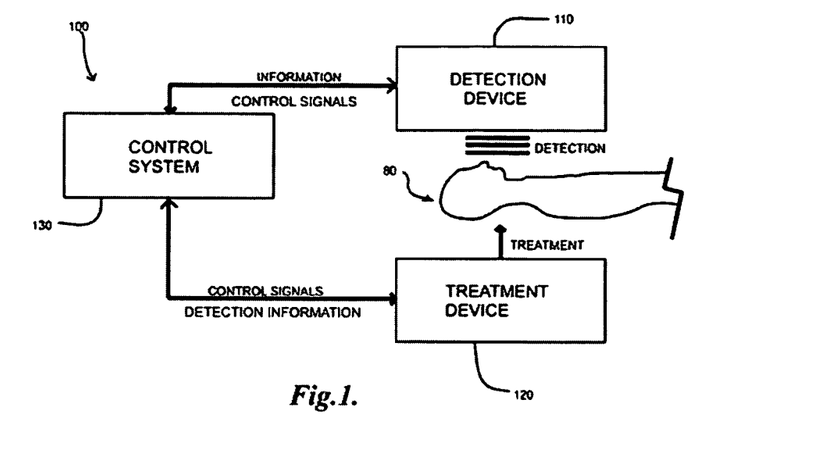
FIG. 1 illustrates a thermal therapy system in one embodiment of the present invention.

In one aspect of the present invention, as shown in FIG. 1, a thermal therapy system 100 includes at least one detection device 110, treatment device 120 and control system 130. In one embodiment, a treatment device 120 may be inserted into and/or in the vicinity of the body 80 of a patient and monitored by the detection device 110 for proper placement near a target tissue. A treatment device 120 may generally be an energy delivery device such as, for example, a laser probe, a radio frequency (RF) probe, a microwave device, an electromagnetic antenna, an ultrasound probe and/or any other appropriate energy delivery device. In general, a treatment device 120 may be selected for compatibility with a given detection device 110 and/or for a particular type of treatment. A detection device 110 may employ, but is not limited to, a magnetic resonance imaging (MRI), ultrasound imaging, X-ray or other electromagnetic imaging, positron emission tomography (PET) imaging, and/or any other appropriate detection modality. In general, a detection modality capable of detecting and mapping temperature changes and/or thermally-induced changes to tissues, and/or providing localized temperature information may be utilized. A detection device 110 or accessory detection device may also be utilized to measure absolute temperature rather than a relative temperature change.

The treatment device 120 may be an energy delivery device in communication with a control system 130 which may also receive information from a detection device 110. The control system 130 may generally act in a feedback response and/or sequential detection manner with the detection device 110 and treatment device 120, if desired, as shown in FIG. 1. The control system 130 may receive information from a detection device 110 that may detect features and changes to the tissues of a patient 80. The control system 130 may then utilize the information to program a treatment and/or monitor the progress of a treatment. For example, the control system 130 may recognize changes in temperature and/or tissue characteristics in the information. The control system 130 may then modulate the energy delivery characteristics of the treatment device 120 such that the treatment is controlled. The control system 130 may also control the detection device 110, such as, for example, for altering the detection settings, altering the detection space or area, changing the detection rate, such as an image capture rate, and/or any other parameter or available setting on the detection device 110.

Figure 1A:
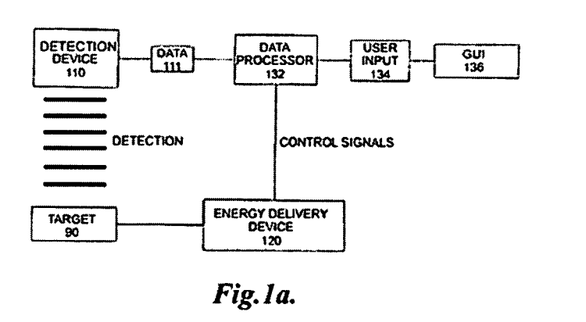
FIG. 1a illustrates another embodiment of a thermal therapy system.

FIG. 1a illustrates a thermal therapy system in accordance with one embodiment of the present invention having one or more detection devices, one or more data processors, and one or more energy delivery devices, and a control system, as well as a method for its use. The thermal therapy system may utilize a detection device to periodically or continuously measure the temperature and/or cell damage of a target receiving energy. In at least one embodiment, a user may input desired parameters to define a control strategy for the energy delivery.

The data processor may use the control strategy to govern the behavior of the energy delivery devices in real time, or near real time, using detection information from the detection device. The data processor may also be capable of displaying images representative of temperature, damage, and/or structure to the user, as well as inputting user-defined parameters, with a graphical user interface (GUI).

A feedback-controlled energy delivery system 200 is illustrated according to one embodiment of the present invention. Energy delivery system 100 includes detection device 110, energy delivery device 120 and control system 130. The control system 130 may include data processor 132. The detection device 110 may use radiation to interrogate a target or other suitable system capable of acquiring temperature and/or other information from a target 90. In one embodiment, target 90 may include biological tissue to be destroyed by heating, and/or any other object having specific localized areas to be heated without damaging surrounding areas. Detection device 110 may include a magnetic resonance device, an ultrasound device, an infrared device, a radio frequency device, x-ray device, infrared detection device, computerized tomography (CT) device, and/or any other appropriate detection modality.

Data processor 132 may include any data processing system capable of receiving and processing data from detection device 110 to control, on a real-time or near real-time basis, the energy delivery device 120. Data processor 132 may include a workstation, personal computer, supercomputer, dedicated hardware, computing cluster and/or any other appropriate device or combination thereof. Energy delivery device 120 may include any device capable of generating heat, or energy that may be transformed to heat, and further capable of conveying this heat or energy to target 90 via one or more applicators, such as in the embodiments described below. Energy delivery device 120 may include a laser device, a microwave device, a resistive heater, radio frequency device, an ultrasound device, a heated fluid device, a radiation source such as an ion beam source and/or any other appropriate device. It may be appreciated that data processor 132 may be either locally or remotely connected to detection device 110 and energy delivery device 120.

In one embodiment of the present invention, detection device 110 may obtain temperature sensitive data 111 on a periodic or continuing basis. The detection device 110 may, for example, transmit temperature sensitive data 111 to the control system 130. The temperature sensitive data 111 may represent the absolute or relative temperature distribution of a point, area plane, contour, or volume of a portion of target 90. For example, a magnetic resonance device may be used to capture data to be processed for determining the structure of selected portions of target 90, as well as the selected portions' relative temperature distribution at a given point in time. After detection device 110 captures data 111 from target 90 for one cycle, data 111 may be either stored in a database in detection device 110 and transmitted at a later time to data processor 132, or the captured data 111 may be immediately sent to data processor 132. It may be appreciated that detection device 110 may pre-process data 111 before it may be transmitted to data processor 132. The detection device 110 and/or the data processor 132 may also include features for motion correction, such as, for example, to compensate for unintended movement of the target 90 within the detection space. The data processor 132 may, for example, also output motion correction information and/or instructions to the detection device 110 for any detected movement of the target 90 such that the detection device 110 may alter or re-orient the detection space and/or otherwise compensate for the movement.

In some embodiments, the control system 130 may actively acquire and/or detect updated data 111 produced by the detection device 110. This may be, for example, desirable with some detection devices, such as MRI scanners, that operate by saving data into a designated file system directory or the like. In one embodiment, a method of obtaining data 111 from real-time and/or near-real-time detection device 110 may include establishing a direct and/or network connection between the detection device 110 and the control system 130, examining the contents of a target file-system directory, and transferring new files appearing in that directory as they become available and/or in a short time thereafter. A direct connection may include, for example, any form of direct electronic and/or wireless connection such as Universal Serial Bus (USB), serial connection, IR connection, wireless fidelity (WIFI), radio connection, and/or any other appropriate connection. A network connection may also be utilized. For example, a file transfer protocol (FTP) connection, a server message block (SMB) protocol connection, a network file system (NFS) protocol connection, Internetwork Packet Exchange/Sequenced Packet Exchange (IPX/SPX) network protocol, token ring network protocol and/or any other appropriate network connection may be utilized.

In some embodiments, the method of acquiring data 111 from the detection device 110 may further include searching for, calculating, computing, and/or determining a target directory on the file system of a detection device 110. The method may also include searching for new files to arrive in that directory. The arrival of new files may be determined by counting the number of files in the directory, comparing a listing of the files in the directory to a previous saved list of the files in the same directory, searching by file update times, and/or any other appropriate method of detecting new files.

The method of computing, calculating, or determining the directory name may include sorting directory names based on time-stamps, sorting based on numeric or alphabetical components of the directory name, or calculating a numeric value which determines the directory name. The directory may also be determined by examining the time stamps of all or some directories and selecting the most recently created and/or most recently accessed. Specific examples of acquiring data 111 from a detection device 110 are discussed below.

In one embodiment of the present invention, data processor 132 may receive data 111 as input data from detection device 110 and processing data 111 to control the operation of the energy delivery device 120 and/or to display information to the user via a graphical user interface (GUI) 136. Some of the information displayed to the user using GUI 136 may include images representative of the temperature of a portion of target 90, the structure of a portion of target 90, the dead and dying cells in a portion of target 90 (where target 90 is biological tissue), and/or any other appropriate information. Other information displayed may include the status of energy delivery device 120, the temperature history of one or more points, areas, contours, planes, or volumes of a portion of target 90, etc. In one embodiment, data processor 132 may also accept user-defined parameters input 134 through GUI 136.

Irreversibly damaged tissue may be displayed using an image representative of damage in GUI 136. A portion of tissue may be considered irreversibly damaged when the cells of the tissue portion are dead, or damaged enough, through protein denaturization, water vaporization, etc., that it is determined, using empirical data, previous experience, or models, that the cells may likely die within a relatively short time span. In one embodiment, a image representative of damage may be constructed using the temperature history for a given portion of tissue. One method of determining tissue damage may utilize temperature history to determine a total amount of heat absorbed by tissue in an area. This may be achieved by keeping a summation of all temperatures measured for a given portion of tissue. If the sum total of heat for the given portion exceeds a predetermined value, the cells in that portion may be considered dead or dying. In one embodiment, the Arrhenius rate equation may be used to calculate irreversible cell damage as a function of the temperature history. The Arrhenius rate equations is commonly expressed as follows: $\Omega = \text{.intg.} A * e - Ea/(RT) \, dt$ Wherein:

A is the frequency factor constant for a given tissue type;

Ea is the activation energy value specific to the type of tissue;

R is the Universal Gas Constant; and

T is the temperature history of the tissue as a function of time; and a cell is considered dead or dying if the value of $\Omega$ is greater than or equal to one when the equation is evaluated.

The Arrhenius rate equation may be integrated with respect to time for a given location of tissue, and if the integrated value is greater than a determined value, then the cells in the location may be considered irreversibly damaged. It may be appreciated that the determined value, based on tissue type, may be a result of empirical analysis, a user's experience, models, or theory. As it may be rare and/or difficult to have a defined, continuous equation for cell temperature as a function of time, the Arrhenius rate equation may be evaluated numerically by using linear and/or non-linear interpolation between temperature history points. It may be appreciated that as the time difference between temperature history points decreases, the degree to which linear and/or non-linear interpolation emulates the real temperature history of a given location of tissue may increase.

Damage distribution data, in addition to (or in place of) temperature data, may be used to determine the control of a treatment device 120. Since the damage to a cell in many cases may be dependent on the properties of the cell type, location, and the like, the appropriate values for constants of the Arrhenius equation may be determined, for example, for a given target. The user may use previous experience, tables, or may load the values from a database or a file. Alternately, the values may be hardcoded into software used by data processor 132, automatically uploaded from a database, and/or otherwise provided. Incorrectly determining the total heat needed may result in charring of the cells if the history of heat received is enough to char the cells or if an absolute maximum temperature is exceeded. Similarly, if not enough heat is absorbed by the cells in tissue, or if a minimum temperature needed to cause cell death or irreversible damage is never reached, the cells may not be dead or dying, although they may be displayed as dead or dying cells in an image representative of damage.

Further exemplary embodiments of a control system, detection device and treatment device relationship may be found in U.S. Pat. No. 6,542,767, the entire contents of which are hereby incorporated by reference.

In an exemplary aspect, the control system 130 controls at least one treatment device 120 to transfer a predetermined amount of energy between the treatment device 120 and at least a portion of a target. In an exemplary embodiment, the control system 130 utilizes information about the target from the detection device 110, which may, for example, contain temperature-sensitive information and/or spatially-resolved information about at least a portion of the target. The control system 130 and/or a user may then determine a preselected amount of energy to transfer between a treatment device 120 and at least a portion of the target based at least in part on the information from the detection device 110. The energy may then be transferred by at least one treatment device 120 and the effect on the target may then be determined by a detection device 110. The control system 130 may further store information on previous energy transfers, such as over the general course of a therapy and/or treatment, and may generally base an amount of energy to be transferred at least in part on previous energy transfer information. Previous information may be stored by the control system 130 in, for example, a memory module and/or other information storage device and/or system. This may be desirable as a transfer of energy may generate a change in a target that may be unexpected. Utilizing previous energy transfer information may then aid in correcting for unexpected events, properties and/or parameters of a therapy and/or treatment.

In some embodiments, the control system 130 may control at least one treatment device 120 to generate multiple energy transfers between the treatment device 120 and at least a portion of a target. Multiple energy transfers may be utilized, for example, to affect a temperature-induced change on at least a portion of a target. In one embodiment, the control system 130 may control a series of stepped energy transfers to, for example, substantially gradually change the temperature of at least a portion of a target. In general, it may be desirable to affect a predetermined temperature change in at least a portion of a target and substantially only to a particular portion of a target. In one example, it may be desirable to change the temperature of a portion of tissue to a predetermined level without substantially changing the temperature of the rest of the tissue to that level. This may, for example, aid in mitigating temperature-induced changes, such as damage, to portions of a tissue outside a target area. Gradual temperature changes may then be utilized to, for example, aid in preventing exceeding a boundary temperature value in at least a portion of a target.

Figure 1B:
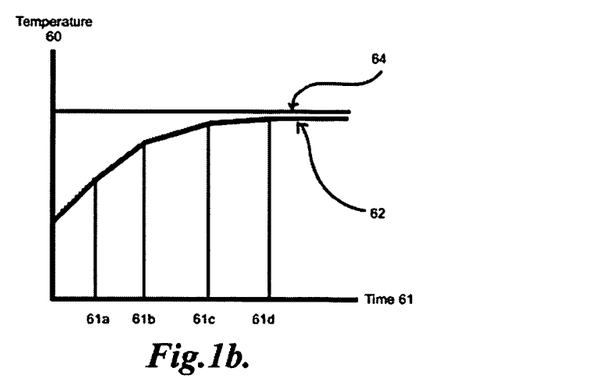
FIG. 1b illustrates a temperature profile utilizing from stepped energy transfers.

In one embodiment, as illustrated in FIG. 1b, a control system 130 may control multiple energy transfers over time 61 at times, for example, 61a, 61b, 61c, 61d. The temperature 60 of at least a portion of a target may, for example, be detected by detection device 110 as temperature profile 62. As described above, a stepped and/or otherwise gradual predetermined energy transfers and the effect may be detected at times, for example, 61a, 61b, 61c, 61d. This may be utilized, for example, to aid in preventing or minimizing temperature from exceeding a given value, such as temperature 64. Such gradual and/or asymptotic approaches to a given temperature value may generally be desirable to aid in minimizing or preventing exceeding a given value, especially when there may be a possibility of reaching the given value between detection steps.

In one exemplary embodiment, the energy delivery in stepwise fashion may be delivered in gradually decreasing energy strength, also in minimizing exceeding a given value.

In general, a thermal therapy system 100 may be utilized to deliver energy to a target tissue such that the tissue may form a lesion by thermally-induced necrosis. This may be useful in treating harmful tissue formations such as, for example, tumors.

In an exemplary embodiment, the treatment device 120 includes a laser with a fluid circulation probe. In general, the probe may include an optical fiber and/or other light transporting medium, and may also include a diffusing and/or targeting element for placement of the energy delivered through the light transporting medium from the laser. The fluid circulation in the probe may be used to affect the temperature of the probe and/or the tissue surrounding the probe by circulating fluid of a desired temperature. The temperature of the fluid may be varied to determine the temperature affect on the probe and/or tissue. The flow characteristics of the fluid and energy output of the laser may be determined by the control system 130 such that it may modulate the energy delivery characteristics of the laser to the tissue.

Figure 2:
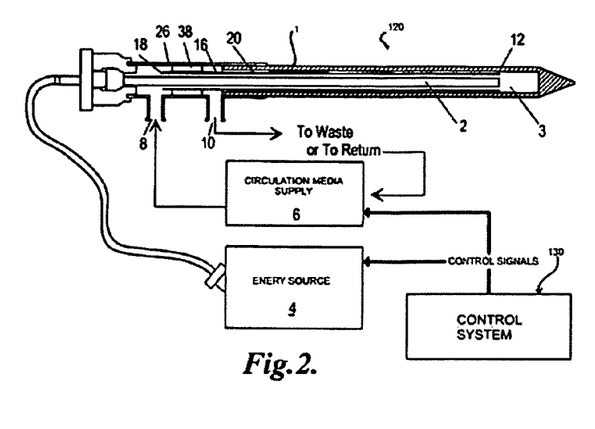
FIG. 2 illustrates an embodiment of a treatment device.

FIG. 2 illustrates an embodiment of an exemplary energy delivery device of a treatment device 120. The treatment device 120 includes an energy delivery apparatus 1, an energy delivery component 2, an energy source 4, and a circulation media supply apparatus 6. The proximal end of the energy delivery component 2 is coupled to the output of the energy source 4. The distal end 3 of the energy delivery component 2 extends within the energy delivery apparatus 1. The circulation medium supply apparatus 6 is connected to the inlet fluid port 8 of the energy delivery apparatus 1. The outlet fluid port 10 is either connected back to the circulation medium supply apparatus 6 (recirculating system) or to a suitable waste collection area (non-recirculating system). The energy source 4 and the circulation medium supply apparatus 6 may be modulated by the control system 130 such that the energy delivery characteristics of the treatment device 120 may be controlled.

In an exemplary embodiment, the energy delivery apparatus 1 includes a housing 12 attached to a coupling assembly 26. A dividing structure 16 separates the lumen of housing 12 into two channels. A first channel 20 is formed between the dividing structure 16 and the housing 12 and a second channel 18 is formed between the energy delivery component 2 and the dividing structure 16. The channels 18 and 20 communicate near or proximate the distal end of the housing 12 to allow fluid to pass from one channel to the other in circulation chamber 3. The channels 18 and 20 may be isolated proximate the coupling assembly 26 to allow fluid to, for example, enter port 8, flow through channel 18, return through channel 20, and exit via the outlet port 10. Also, in other embodiments, the fluid may flow in the opposite direction. In this manner, counter current circulation media flow cools the housing 12, the dividing structure 16, the energy delivery component 2, and the surrounding tissue. In the above exemplary embodiment, the dividing structure 16 is depicted as tubular and the channels 18 and 20 are depicted as annuli or concentric flow paths. However, various shaped dividing structures 16 or shaped housings 12 may be used to form channels. As such, the tube-like structures, 12 and 16, may have cross-sectional shapes such as stars, squares, triangles, ovals, circles, and other shapes. Multiple annuli or concentric flow paths may also be utilized using multiple dividing structures.

Figures 2A, 2C:
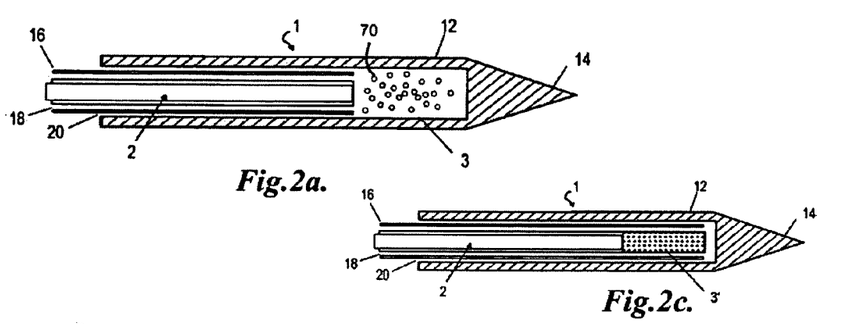
FIGS. 2a and 2b illustrate the use of a scattering material with a treatment device.
FIGS. 2c, 2d and 2e illustrate embodiments of treatment devices with energy directing components.
Figure 2B:
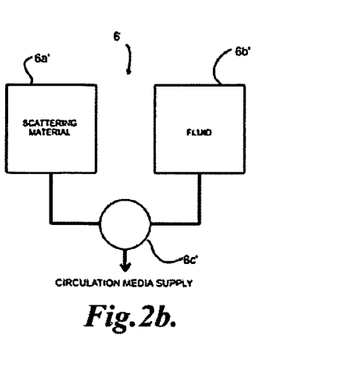
Figures 2D, 2E, 2F:
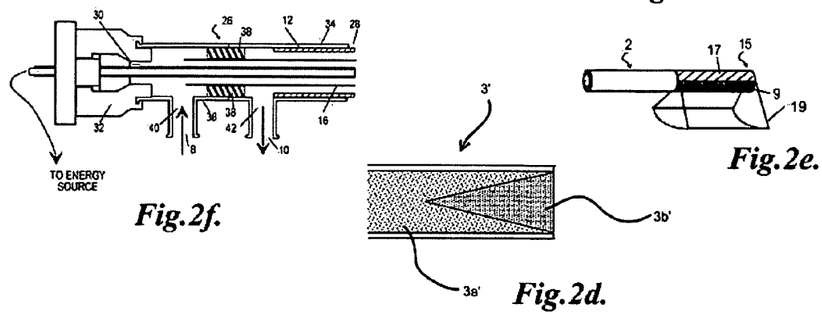
FIG. 2f illustrates a coupling assembly of a treatment device.

The coupling assembly 26, as illustrated in FIGS. 2 and 2f, may include the inlet fluid port 8, outlet fluid port 10 and an opening 30 for introducing an energy delivery component 2. An example of a coupling assembly 26 may be formed by mating two male-female taper luer tees, such as part# LT878-9, Value Plastics, Inc. A male Touhy Borst connector 32, such as part#80344 Qosina, may be included to provide a substantially leak-proof seal at the energy delivery component opening 30 and for securing the energy delivery component 2 to the coupling assembly 26. The distal segment 34 of the coupling assembly is bonded to the outer housing 12 to create a fluid tight seal. A proximal section 36 of coupling assembly 26 contains a seal 38 between the inner tubular structure 16 and the proximal section 36 to prevent fluid communication between inlet fluid port 8 and outlet fluid port 10 within the coupling assembly 26. Both distal and proximal seals and other bonds may be created using a suitable UV cure epoxy, such as Part#140-M, Dymax Corp. Alternative methods of bonding and sealing may be used including various cyanoacrylates, epoxies, silicones, heat bonds, press fits, and threaded assemblies, among other methods. Solvent bonding may also be used to mount the tubular structure 16 into the coupling assembly 26. In general, one or more solvents of the materials of the components may be utilized to partially dissolve the joining surface(s), which may then join together as the solvents evaporate and/or otherwise dissipate. It is contemplated that the opening 30 and one of inlet fluid port 8 or outlet fluid port 10 may be coincident.

In one exemplary embodiment, the energy delivery apparatus 1 and the energy delivery component 2 are integrated or assembled just prior to insertion into the tissue. In another exemplary embodiment, the energy delivery apparatus 1 and the energy delivery component 2 are integrated or assembled during manufacture prior to being delivered for use.

The energy delivery apparatus 1 includes a flexible outer housing 12 having a tubular structure along its length and a penetrating tip 14 at its distal end. The outer housing 12 may, for example, be rigid enough to penetrate soft tissue without kinking, yet be flexible enough to follow curved or arcuate paths. The solid penetrating tip 14 may take the form of a cutting edge or a point, among others. The housing 12 contains an inner tubular structure 16 within its lumen that extends between a proximal end and a distal end of the outer housing 12. The inner tubular structure 16 may be centered within the housing 12 to create fluid inlet lumen 18, and fluid outlet lumen 20. The inlet and outlet lumens (18 and 20) facilitate delivery and return of circulation media (e.g. water, saline, or carbon dioxide, among others) to and from the distal end of the energy delivery apparatus 1. The fluid inlet lumen 18 facilitates housing of the energy delivery component 2. Suitable materials for the flexible outer housing 12, and inner tubular structure 16 include flexible radio-opaque and non radio-opaque medical grade plastic tubing, such as polycarbonate (Makrolon, Bayer Polymers), polyurethane, polyethylene, polypropylene, silicone, nylon, polyvinylchloride (PVC), polyethylene terephthalate (PET), polytetrafluoroethylene (PTFE), acrylonitrile butadiene styrene (ABS), polyether sulphone (PES), polyetheretherketone (PEEK), fluorinated ethylene propylene (FEP), other biocompatible polymers, or any combination thereof.

The energy delivery component 2 disposed within the fluid inlet lumen may include one or more optical waveguides positioned to direct light through both the inner tubular structure 16 and outer housing 12. In some embodiments, the energy delivery component 2 may be movable relative to the energy delivery apparatus 1, for example, translating along the axis of the energy delivery apparatus 1. Energy emitted the energy delivery component 2 may pass through transparent housing 12 and structure 16. More than one region of tissue located along the housing 12 may be treated by moving the energy delivery component 2. Further examples of exemplary treatment devices are described in U.S. Pat. No. 7,270,656, the entire contents of which are hereby incorporated by reference.

In some embodiments, the circulating fluid may be utilized to cool the probe and the surrounding tissue. This may be useful in protecting the probe from thermal damage and may also be utilized to help minimize carbonized tissue formation around the probe during treatment, such that the energy being delivered may reach further from the probe.

In other embodiments, the circulating fluid may also be utilized to raise the temperature of the tissue surrounding the probe before and/or during treatment such that, for example, the tissue may reach a given temperature faster during energy delivery by the probe. The temperature may also be raised if the control system 130 determines that insufficient heating is occurring in the tissue to affect treatment.

The fluid may be circulated at a constant rate or it may be circulated at a variable rate, which may include periods of no circulation, during the course of a treatment. The temperature of the fluid may also be varied during the course of a treatment.

In some embodiments, the circulation media supply apparatus 6 may deliver a fluid with light scattering properties. In one embodiment, the circulation media may have a high refractive index such that light from the energy delivery component may be scattered at angles diverging from the generally longitudinal axis of the housing. In an exemplary embodiment, the circulation media may include at least one scattering material 70, as shown in FIG. 2a, which may be held in solution or suspension in the circulation media. The scattering material 70 may be, for example, a particulate material that may be dispersed within the circulation media. The circulation media may then be utilized to scatter light from the energy delivery component 2 in the circulation chamber 3 and/or other portions of the energy delivery apparatus 1. In general, the physical properties of the scattering material 70 may be selected to provide desired scattering characteristics. For example, the size of a particle may be changed to yield a different degree of scattering. As a further example, the solubility or the ability of a substance to stay in suspension may also be utilized to produce desired scattering characteristics. Appropriate materials for a scattering material may include, but are not limited to, plastics, metals such as gold, platinum, silver, aluminum and copper, glasses, metal oxides such as titanium dioxide, zinc oxide and alumina, silica or silicates and/or any other appropriate scattering material or combination thereof. The scattering material 70 may generally be provided in the circulation media at an appropriate concentration to effect scattering of light from the energy delivery component 2. The scattering material may come, for example, premixed with the circulation media and may also be reused during a procedure. In an exemplary embodiment, a circulation media supply apparatus 6' may include a scattering media reservoir 6a', a fluid reservoir 6b' and a mixing unit 6c' which may mix the scattering material 70 with the circulation fluid, as shown in FIG. 2b. The mixing unit 6c' may also be controlled by the control system 130 such that the degree of scattering may be altered to affect the energy delivery characteristics of the treatment device.

Other embodiments of dynamic scattering devices and methods are provided in U.S. patent application, Ser. No. 12/176,310, filed Jul. 18, 2008, entitled "LIGHT DIFFUSING FIBER AND METHOD OF USE", the entire contents of which are hereby incorporated by reference.

In other embodiments, the energy delivering apparatus 1 may include a scattering or diffusing element. FIG. 2c illustrates an embodiment of an energy delivering apparatus 1 which may include an element 3' that may substantially scatter, diffuse and/or direct the energy from the energy delivery component 2. The element 3' may, for example, include a solid, gel, semi-solid, emulsion, solution, liquid, suspension and/or any other appropriate scattering, diffusing, energy directing and/or other energy modifying substance or combination thereof. The element 3' may further be coupled to the end of energy delivery component 2. In some embodiments, the element 3' may include multiple regions of substantially different properties, such as illustrated with the element 3' of FIG. 2d with first region 3a' and second region 3b'. The energy delivery apparatus 1 may also include an energy directing element, such as element 15 which may receive energy from energy delivery component 2 in FIG. 2e. As illustrated, for example, a region 17 of the element 15 may substantially block, reflect, redirect and/or otherwise prevent energy from exiting the element 15 on at least a portion of the element 15. As illustrated, for example, the energy may then exit 19 through an energy permeable portion 9.

Other exemplary embodiments of energy diffusing, scattering and/or modifying elements are provided in U.S. Pat. No. 7,274,847, the entire contents of which are hereby incorporated by reference.

In some embodiments, the temperature in the locality of the tissue for treatment may be altered by altering the temperature of the circulatory flow and/or surrounding tissue. Raising the temperature of the tissue may also generally enhance the size of the ablated volume as a smaller increase in temperature may be desired by energy delivery from the treatment device, particularly at distances further away from the treatment device. This may be accomplished through a variety of methods, which may include, but are not limited to, introducing temperature controlled fluid into the circulatory flow, such as through a nearby blood vessel, altering the temperature of the circulatory flow by contact with a closed temperature controlled object, such as a closed catheter, contacting the nearby tissue with a temperature controlled object or material, such as a hot or cold pad, and/or any other appropriate method. For example, a temperature controlled energy delivery device and/or heating element may be placed in a blood vessel which may be in proximity to and/or supply a tissue for treatment.

Also, the circulatory flow may be blocked and/or diverted from a tissue area for treatment and a sterile, biocompatible temperature-controlled fluid may be introduced into the vasculature in place of the normal circulatory fluid. In some embodiments, a fluid with more desirable optical and/or thermal qualities than the normal circulatory fluid, such as blood, may be utilized. For example, a fluid with lower absorption and/or higher transmission of energy from a treatment device may be utilized to increase the amount of energy delivered to the target tissue and decrease the amount of energy absorbed by surrounding fluid. This may be useful and/or desirable in situations where there is a large quantity of circulatory fluid, such as, for example, in the liver, where it is desirable to deliver as much energy as possible to the tissue for treatment rather than energy being absorbed and/or diffused by the circulatory fluid. This may also enable higher power energy sources to be utilized with decreased effect on the surrounding tissues, especially through energy absorption by the circulatory fluid.

In yet other embodiments, the treatment device may include materials of high thermal conductivity. The treatment device may thus be temperature controlled by application or removal of energy at a portion remote to the target area, where the high thermal conductivity material may be utilized to appropriate distribute the temperature control along the treatment device. The treatment device may also incorporate features for increasing its thermal conductivity, such as, for example, heat transfer elements which may include, for example, heat pipes and/or other elements that enhance thermal conductivity.

Figure 3:
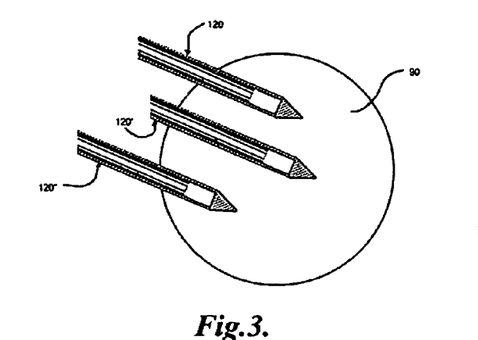
FIGS. 3, 3a and 3f illustrate the use of multiple treatment devices.

In still other embodiments, the thermal therapy system 100 may incorporate multiple treatment devices. The treatment devices may be controlled as a group or they may be individually controlled. The treatment devices may be spatially oriented in or near a tissue for treatment and may be utilized to affect treatment in a spatially controlled manner, an example of which is illustrated in FIG. 3 with treatment devices 120, 120', 120" and target 90. The treatment devices 120, 120', 120" may, for example, be targeted in particular directions for coverage of a target 90. The treatment devices 120, 120', 120" may also be controlled in a temporal manner by controlling the activation and/or modulation of each device in a time-dependent manner. This may be useful, for example, in controlling lesion formation by increasing energy delivery in a given region of the treatment volume and/or decreasing energy delivery in another region. This may aid in creating more uniform lesions, decreasing overall treatment time and in avoiding char formation due to excess energy delivery. Multiple treatment devices may also be useful in controlling lesion shape. Any appropriate number of treatment devices may be utilized.

In an exemplary embodiment, the multiple treatment devices may be laser probes with fluid circulation and may be individually modulated by the control system 130. The laser probes may, for example, be spatially oriented in or near a tissue for treatment to optimize and/or increase the volume being treated. This may be used, for example, to increase the overall size of a thermally generated lesion. Each laser probe may also be targeted such that energy delivery may be substantially confined to a given volume. This may be accomplished with, for example, directional laser probes which may deliver light energy in a particular general direction rather than, for example, diffusing energy in all directions. The fluid circulation characteristics of each laser probe may also be individually modulated, as discussed above. The multiple probes may also be utilized to generate a base temperature profile or gradient in the target by circulating fluid of different temperatures through each probe.

Figure 3A:
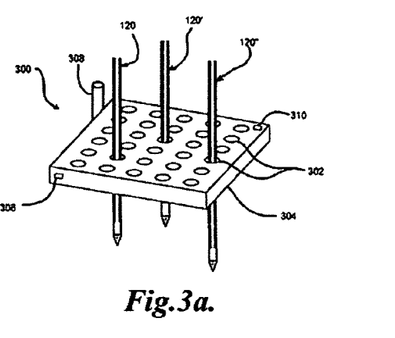

In some embodiments, multiple treatment devices may be placed in or near a treatment by use of a guide. A guide, for example, may be utilized to aid in a substantially repeatable or more precise placement of each treatment device. FIG. 3a illustrates an example of a guide 300 which may be utilized with multiple treatment devices, such as treatment devices 120, 120', 120" as shown. The guide 300 may include, for example, a plurality of holes 302 in the guide body 304, any of which treatment devices 120, 120', 120" may be inserted through such that each treatment device may be directed to a particular site in the target. In an exemplary embodiment, the guide 300 may also include features for aiding in positioning and directing of treatment devices to the proper location. For example, at least one fiducial marker may be utilized to aid in positing and/or orienting of the guide 300 and/or treatment devices, such as devices 120, 120', 120". A fiducial marker may generally be a feature, formation, device, portion of a device, and/or any other appropriate object or form that may be detectable by a detection device that may be in a substantially known and fixed spatial relationship to another object or form, such as the guide 300. Also, at least one fiducial marker may be utilized to resolve the position and/or orientation of the guide 300, such as, for example, by providing an appropriate number of reference points to form a plane which may have a known and fixed spatial relationship with the guide 300. At least one fiducial marker may also include a form or shape that may have a detectable unique or semi-unique cross-section such that it may be indicative of position and orientation of an intersecting detection plane of a detection device, such as an MRI slice. In general, detection of a fiducial marker by a detection device, such as, for example, an MRI, CT and/or any other appropriate substantially computer-controlled detection device, may utilize region growing methods to substantially detect the entire fiducial marker. In one embodiment, the guide 300 may include fiducial markers 306, 308, 310, which may be utilized to resolve the position and orientation of the guide 300 in space and/or to a target volume using a detection device. A control system may utilize the known dimensions of the guide 300 and the known positions of the fiducial markers 306, 308, 310, both in space and their fixed positions relative to the guide 300, to project the trajectory of the holes 302, such that treatment devices may be properly placed through selected holes 302. This may include, for example, providing the insertion depth and insertion angle into the hole 302, if applicable. The control system 130 may also calculate and prescribe a reorientation the guide 300 for better placement of treatment devices. In general, the fiducial markers may be selected to appear on a given detection modality, such as, for example, water under MRI or metallic objects under X-ray. A guide 300 may also include features for enhancing the contrast of the holes 302 such that they may be better detected by the detection device. This may also be useful for guiding treatment devices to the holes 302. Contrast enhancing agents for particular detection modalities may be utilized. The guide 300 may also include temperature controlled fiducial markers which may be resolved through temperature detection. This may be useful as the detection device for a thermal therapy system 100 may generally include detection for localizing temperature changes and/or absolute temperatures within a detection volume.

Figure 3B:
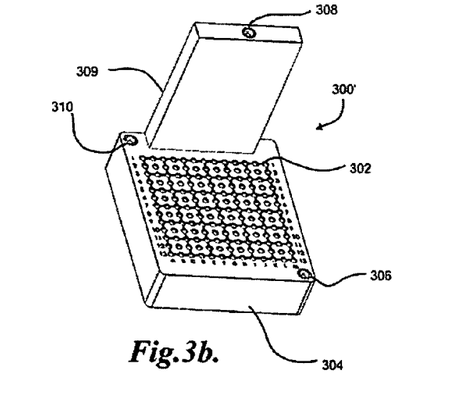
FIGS. 3b and 3e illustrate embodiments of multiple treatment device guides.
Figure 3C:
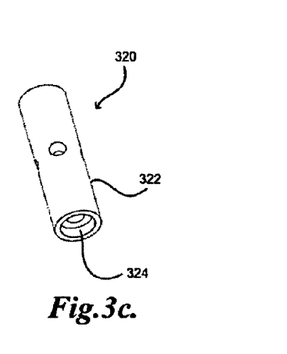
FIGS. 3c and 3d illustrate embodiments of fiducial markers.
Figure 3D:
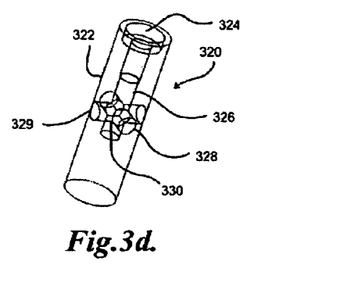
Figure 3E:
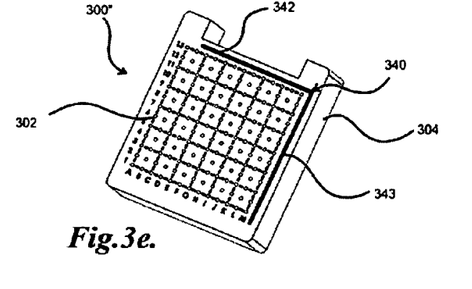
Figure 3F:
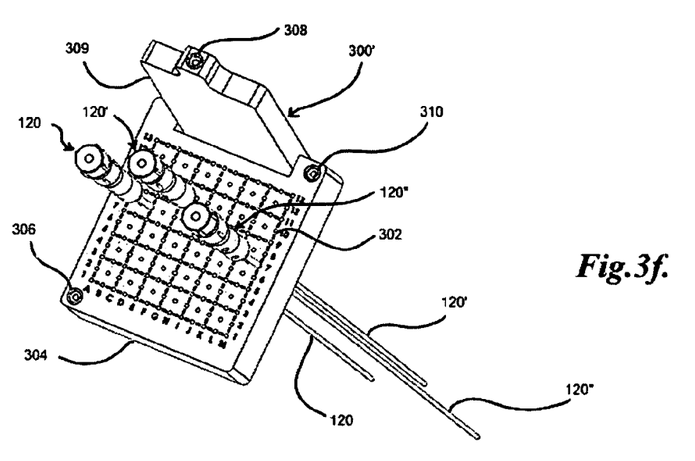

An exemplary embodiment of a guide 300' is illustrated in FIG. 3b, which may be utilized with multiple treatment devices, such as treatment devices 120, 120', 120" as shown. The guide 300' may include, for example, a plurality of holes 302 in the guide body 304, any of which treatment devices 120, 120', 120" may be inserted through such that each treatment device may be directed to a particular site in the target, as illustrated in FIG. 3f. The guide 300' may further include an extension 309 which may be, for example, utilized for mounting and/or positioning the guide 300'. The extension 309 may further be adjustable, such as, for example, adjustable for angle between it and the guide body 304. The guide 300' may further include at least one fiducial marker, such as fiducial markers 306, 308, 310. The markers may be integral to the guide 300' or they may also be separable. FIGS. 3c and 3d illustrate an example of a separable fiducial marker 320, which may, for example, be any or all of the fiducial markers 306, 308, 310 of FIG. 3b. The fiducial marker 320 may generally include a body 322 and a cavity 324. The cavity 324 may generally be filled with a material visible to a detection device, such as, for example, water for MRI, metal for X-ray, and/or any other material appropriate for a given detection device. The cavity 324 may further be sealed and/or otherwise closed off to substantially retain a material. In one embodiment, as shown in the see-through of FIG. 3d, the cavity 324 may include a central channel 326 and may further include cross channels 328, 329. This may be desirable as it may generally increase the detectable volume of the fiducial 320 and may also generate a substantially discrete point for positioning reference, such as the intersection 330 of the channels 326, 328, 329. In general, it may be desirable for the fiducial marker 320 to be reusable and sterilizable.

In another embodiment, a guide 300" may include at least one fiducial marker that may substantially and independently define a plane. FIG. 3e illustrates an example of a guide 300" with a body 304 and a plurality of holes 302. The guide 300" may further include a fiducial marker 340, which may substantially define a plane. For example, as illustrated, the fiducial marker 340 may include 2 linear segments 342, 343. It may be generally appreciated that any appropriate geometric form and/or combination of forms that may define a plane may be utilized.

In another aspect of the invention, the control system 130 of the thermal therapy system 100 may incorporate predictive and/or adaptive treatment modulation. In one embodiment, the control system 130 may generate a predictive model of a treatment based on known and/or assumed parameters, and may calculate an appropriate treatment course, such as, for example, applying energy to a tissue at a particular rate and/or duration based on the predicted model. The control system 130 may then monitor the progress of treatment by receiving information from a detection device 110, and may then adapt to the measured progress of the treatment by entering and/or altering parameters in the predicted model to aid in generating a more accurate model, after which the control system 130 may apply a modulation to the treatment, such as, for example, an alteration to the energy delivery characteristics of a treatment device 120. In some embodiments, the control system 130 may, based on a model and available data, make a preemptive action ahead of received data. This may be useful, for example, when utilizing a detection device 110 where there is a delayed receipt of data by the control system 130. The control system 130 may, for example, determine that a treatment should stop due to a predicted temperature over a designated limit in the target. This may aid in minimizing damage outside of the target due to data lag.

In yet another aspect of the invention, the thermal therapy system 100 may incorporate safety systems. In one embodiment, the control system 130 of a thermal therapy system 100 may shut down the treatment device 120 and/or warn the user of a detected safety parameter. The control system 130 may, for example, shut down the treatment device 120 in response to a detected temperature above a given level in the information provided by a detection device 110. This may be useful in detecting failures in a treatment device 120, such as, for example, a laser light transport medium breaking and/or otherwise overheating past a design limitation. This may also be useful in detecting unintended temperature changes in the target, such as, for example, unintended temperature increases in a tissue area outside the target area. Other safety features, such as, for example, temperature sensors, specific light wavelength detectors and/or any other safety features may also be incorporated.

Figure 4:
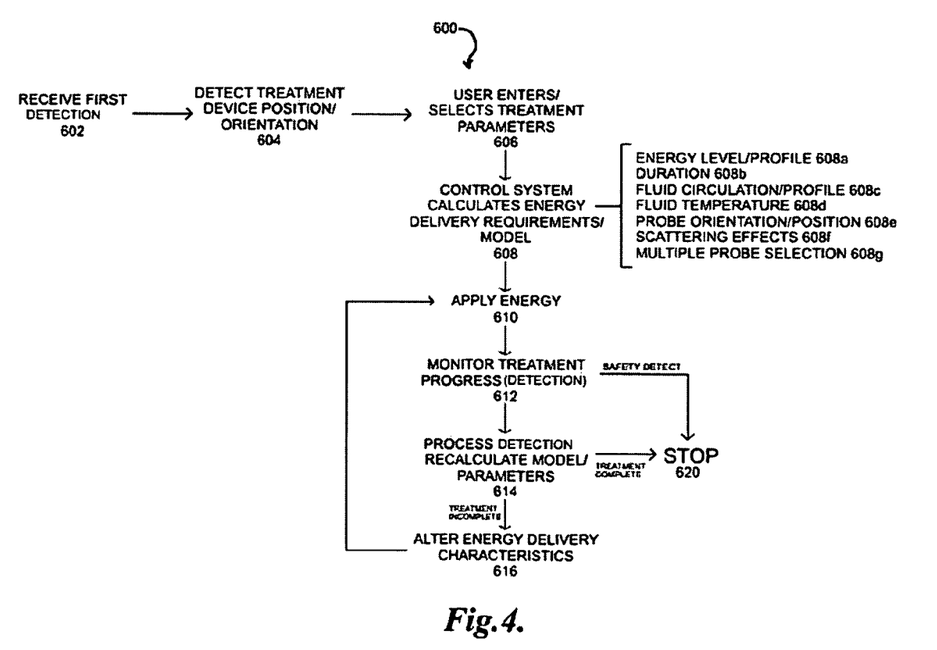
FIG. 4 is a flow diagram of a method of use for a thermal therapy system.

Referring to FIG. 4, a method 600 for utilizing real-time or near real-time feedback, and/or sequential detection to control an energy delivery system 100 is discussed according to one embodiment of the present invention. In step 602, detection device 110 may obtain data 111 from measurements conducted on target 90 for use as initial reference data for data processor 132. This initial reference data may be utilized to develop an initial image representing, for example, magnitude, temperature, and/or damage. The initial reference data may also be used to develop an initial reference temperature distribution in implementations where detection device 110 may only capable of detecting temperature differences, rather than absolute temperature, such as, for example, MRI thermometry and/or other forms of temperature detection.

In step 604, the control system 130 may detect the positions and/or orientations of the treatment device(s) 120 in the data 111 to aid in proper placement and targeting of the treatment. The user may then enter and/or select treatment parameters, such as, for example, treatment boundaries and threshold temperature at those boundaries, in step 606. The control system 130 may then calculate the energy delivery requirements for the treatment in step 608. This may include, but is not limited to, selecting the amount of energy and/or energy profile for delivery 608a, the treatment duration 608b, fluid circulation rate/rate profile 608c and fluid temperature 608d in a fluid circulation treatment device, the orientation/position of the treatment device 608e, which may include the adjustment of a component within the treatment device such as the translatable energy delivery component described above, scattering effects 608f, such as, for example, circulating scattering material in the circulation fluid, the utilization and settings of multiple treatment devices 608g, which may include the detection of, projection through and/or reorientation of a guide, and/or any other appropriate parameters, such as the numerous examples of adjustment and/or modulation provided above. The user may also manually input and/or alter the parameters determined by the control system 130.

In general, the control system 130 may calculate, based on available information, an optimized treatment plan which the user may accept or alter. An optimized treatment plan may in general maximize the irreversible damage to a target area while minimizing the damage to other areas. The optimization may also in general reduce and/or prevent the formation of charred tissue and/or otherwise undesirable treatment effects. Such automatic optimization tuning may be desirable as a given thermal therapy system 100 may incorporate multiple parameters which may exceed the level of easy and/or expedient consideration by a user and may take full advantage of the processing and calculation abilities of an assisted control system, such as by a computerized system. Automatic optimization tuning may thus take advantage of changeable characteristics in the thermal therapy system rather than attempting to optimize a treatment while working around otherwise unaltered characteristics of the system. The automatic optimization may also become increasingly more useful as more devices and tools become available with controllable parameters and/or settings. Also, the user may also apply limitations on any of the available parameters and/or settings for further control of the optimization scheme. For example, a user may apply a time limitation for the treatment plan to accommodate a patient and/or limitations on the usage of equipment. It may be appreciated that a wide array of situations and/or conditions may be accommodated for through use of a highly adjustable, automatic optimization for a treatment, which may aid in streamlining the overall treatment experience.

After generating an optimized treatment plan, the system may then proceed to apply energy for the treatment in step 610. This may include activating and modulating the energy source of a treatment device 120, such as a laser, as well as activating and modulating the other elements of the system, such as a circulation media supply apparatus. The control system 130 may then monitor the progress of the treatment in step 612 through data from the detection device 110, which may be operating in real-time and/or near real-time (e.g. a new dataset every few seconds), or in a sequential detection manner, such as prior to energy delivery and immediately after energy delivery. The control system 130 may also detect and/or compensate for motion in the target, such as, for example, by controlling the detection device to correct for motion in the target and/or processing the data from the detection device to account for motion correction. If during monitoring the control system 130 detects a safety concern, it may automatically proceed to a STOP command 620, which may halt the delivery of energy to the target, and it may alert the user of the concern. The user may also utilize the STOP command 620 at any time. The control system 130 may also utilize an external temperature monitor as a control. For example, a separate temperature monitor, such as a thermometer or other temperature sensor, may be placed within the detection space of the detection device 110. The control system 130 may then compare the temperature measured by the external temperature monitor with the temperature determined from the detection device 110. This may be utilized to correct for temperature errors, such as, for example, with temperature detection devices that only measure relative temperature changes rather than absolute temperature.

The control system 130 may continuously process data received from the detection device to recalculate the requirements of the treatment in step 614. If the treatment is determined to be incomplete, e.g. the boundaries selected in the target have not reached a given temperature, the control system 130 may alter the energy delivery characteristics of the treatment using the data feedback and/or sequential detection from the detection device 110 at step 616. The control system 130 may also determine that no alterations are necessary. The system may then apply energy to the target at step 610 utilizing the new or unchanged parameters. This cycle may continue until the treatment is determined to be complete or manually halted, after which it may proceed to the STOP command 620.

Example of Acquiring Data from a Detection Device 1

For example, in communicating with a GE scanner running the LX operating system, a method for acquiring data from the device may include:

1) connecting to the scanner using an FTP connection protocol;
2) listing all or some of the files found in the /export/home1/sdc_image_pool/mri_scan directory (or other equivalent directory or link thereto);
3) sorting the all or some of the returned file names to determine the largest first number in any of the file names;
4) determining a first filename;
5) checking the size and/or execute status of the file permission for a file with the first determined filename;
6) requesting retrieval of the first file with the first determined file name as soon as the execute permission has been set positively and/or the file size indicates the file is complete;
7) receiving the first file with the first determined filename;
8) determining a next filename; and
9) performing steps 5-8 above repeatedly for as long as is desirable.

Example of Acquiring Data from a Detection Device 2

For example, in communicating with a GE scanner running the EXCITE operating system, a method for acquiring data from the device may include:

1) connecting to the scanner using an FTP connection protocol;
2) listing all or some of the files or directories found in the /export/home1/sdc_image_pool/images directory (or equivalent directory or link thereto);
3) sorting the all or some of the returned file or directory names to determine a most recent directory name;
4) determining a first filename and determined directory location;
5) checking the existence of the first determined filename in the determined directory location;
6) requesting retrieval of the first file with the first determined file name as soon as it exists;
7) receiving the first file with the first determined filename;
8) determining a next filename; and
9) performing steps 5-8 above repeatedly for as long as is desirable.

Example of Acquiring Data from a Detection Device 3

For example, in communicating with a Siemens scanner running the Syngo application within the Windows® operating system, a method for acquiring data from the device may include:

1) connecting to the scanner using an FTP or SMB connection protocol;
2) obtaining a listing of all directory names within a given directory;
3) determining a most recent directory based on most recent file access or modification time-stamp;
4) obtaining a listing of all files in the determined most recent directory and comparing that listing to a listing of files which have already been retrieved onto the local machine;
5) determining the names of files which exist on the scanner but which have not yet been retrieved onto the local machine;
6) determining the order in which the files should be retrieved based on examination of the determined file names;
7) retrieving those files using an FTP or SMB protocol network connection;
8) waiting a specified amount of time; and
9) performing steps 4-8 above repeatedly for as long as is desirable.

Example of Acquiring Data from a Detection Device 4

For example, in communicating with a Siemens scanner running the Syngo application within the Windows® operating system, a method for acquiring data from the device may include:

1) connecting to the scanner using an FTP or SMB connection protocol;
2) determining a target directory on the scanner filesystem;
3) determining the current clock date and time on the scanner system;
4) determining a filename component based on the determined date and time;
5) obtaining a listing of all files in the determined target directory conforming to or containing the determined filename component;
6) determining the order in which the listed files (if any) should be retrieved based on examination of the filenames obtained via the listing;
7) retrieving those files using an FTP or SMB protocol network connection;
8) waiting a specified amount of time; and
9) performing steps 4-8 above repeatedly for as long as is desirable.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A system for thermal therapy comprising:
   at least one detection device for generating data on the thermal energy characteristics of a target area;
   at least one treatment device for transferring a preselected amount of energy between it and at least a portion of said target area, the at least one treatment device having,
      a housing extending from a proximal end to a distal end along a longitudinal axis,
      a circulation chamber at the distal end of the housing,
      a tubular dividing structure concentric to the longitudinal axis defining a first annular channel and a second annular channel that extend from the proximal end to the circulation chamber, a first access port at the proximal end and in fluid communication with the first annular channel, a second access port at the proximal end and in fluid communication with the second annular channel, the first and second annular channels in fluid communication at the circulation chamber at the distal end of the housing;

at least one treatment device guide comprising a plurality of channels in a guide body, an extension plate adjustably coupled to said guide body at a plurality of adjustable angles between the extension plate and the treatment device guide, where the extension plate is configured to mount or position the treatment device guide, at least one fiducial marker on the guide, and at least one fiducial marker on the extension plate, each of said plurality of channels is adapted for retaining the at least one treatment device; and at least one control system adapted for communicating with said at least one detection device and said at least one treatment device, said control system determining said preselected amount of energy based at least in part on said data;

wherein said control system receives the data from said at least one detection device and communicates with said at least one treatment device to transfer the preselected amount of thermal energy between the treatment device and at least a portion of the target area to substantially affect a predetermined change in the thermal characteristics of said at least a portion of said target area to an extent determined by said detection device.

2. The system of claim 1, further comprising a memory module for storing data about at least a previous preselected amount of thermal energy determined by the control system.

3. The system of claim 2, wherein said control system determines said preselected amount of energy based at least in part on said data and said data about previous preselected amount of energy stored in said memory module.

4. The system of claim 1, wherein said at least one treatment device comprises capabilities of delivering energy to and removing energy from at least a portion of said target area.

5. The system of claim 1, wherein said at least one treatment device comprises multiple devices for simultaneous transferring of energy between said devices and at least a portion of said target area.

6. The system of claim 1 wherein said housing includes a coupling assembly coupled to the housing opposite the distal end, the coupling assembly comprising an opening for positioning an energy delivery component extending along the longitudinal axis; and the tubular dividing structure located within the housing and forming the first annular channel between the tubular dividing structure and the housing and the second annular channel between the tubular dividing structure and said energy delivery component.

7. A system for detection guided therapy of a target area comprising:

at least one detection device;

at least one treatment device;

at least one treatment device guide comprising a plurality of channels in a guide body, an extension plate adjustably coupled to said guide body at a plurality of adjustable angles between the extension plate and the treatment device guide, where the extension plate is configured to mount or position the treatment device guide, and at least one fiducial marker, each of said plurality of channels is adapted for retaining one of said treatment device; and at least one control system in communication with said at least one detection device and said at least one treatment device;

wherein said at least one fiducial marker is detectable by said detection device and said control system resolves at least a location and orientation of said treatment device guide relative to at least a portion of said target area at least partially based on the detection of said at least one fiducial marker;

wherein the at least one fiducial marker includes at least one fiducial marker on the guide and at least one fiducial marker on the extension plate.

8. The system of claim 7 wherein each of said plurality of channels is adapted for guiding said at least one treatment device to a preselected portion of the target area at least partially based on the location and orientation of said guide relative to the target area.

9. The system of claim 7, wherein said at least one treatment device is selected from the group of an energy transfer device, a biopsy device, an injection device and a target access device.

10. The system of claim 7, further comprising resolving the orientation and position of said at least one fiducial marker relative to at least a portion of said target, wherein the resolved orientation of said at least one fiducial marker is indicative of the orientation of said guide.

11. The system of claim 7, wherein said at least one fiducial marker comprises a three-dimensional form with at least a semi-unique cross-sectional shape indicative of position and orientation of an intersecting detection plane of an MRI slice.

12. The system of claim 8, wherein each of said plurality of channels defines a trajectory determined by said control system using at least in part the location and orientation of said guide relative to said target.

13. The system of claim 6, wherein the energy delivery component includes at least one optical wave guide positioned to direct light through the housing.

14. The system of claim 13, further comprising an energy diffusing element positioned within the circulation chamber and adjacent the energy delivery component.

15. The system of claim 6, wherein the energy delivery component includes an energy directing element having a first region configured to prevent energy from exiting the energy delivery component and a second region having an energy permeable portion configured to enable energy to exit through the energy permeable portion.

16. The system of claim 7, wherein the at least one fiducial marker on the guide includes two intersecting linear segments to define a plane of the guide.

17. The system of claim 7, wherein the at least one fiducial marker includes a body defining a cavity having a central channel and a plurality of intersecting cross channels filled with a material visible to the detection device.

18. A system for detection guided therapy of a target area comprising:

a plurality of treatment devices, each treatment device configured to deliver energy to at least a portion of a target; and a treatment device guide defining a plurality of guide holes, each guide hole configured to receive one of the plurality of treatment devices to guide the treatment device to the target, the treatment device guide including, an extension plate adjustably coupled to the treatment device guide and configured for positioning the treatment device guide relative to the target, the extension plate configured to adjustably position the treatment device guide at one of a plurality of adjustable angles relative to the extension plate, a first fiducial marker attached to the treatment device guide, and a second fiducial marker attached to the extension plate, wherein the first and second fiducial markers are configured to aid in positioning the device guide and the plurality of treatment devices relative to the target.

19. The system of claim 18, wherein at least one of the treatment devices is a laser probe having:

a housing extending from a proximal end to a distal end along a longitudinal axis;

a circulation chamber at the distal end of the housing;

a tubular dividing structure concentric to the longitudinal axis defining a first annular channel and a second annular channel that extend from the proximal end to the circulation chamber;

a first access port at the proximal end and in fluid communication with the first annular channel;

a second access port at the proximal end and in fluid communication with the second annular channel, the first and second annular channels in fluid communication at the circulation chamber at the distal end of the housing.

* * * * *